United States Patent [19]

Fox

[11] 4,062,237
[45] Dec. 13, 1977

[54] CROSSED BEAM ULTRASONIC FLOWMETER

[76] Inventor: Martin D. Fox, 1 Storrs Height Road, Storrs, Conn. 06268

[21] Appl. No.: 684,286

[22] Filed: May 7, 1976

[51] Int. Cl.$^2$ .............................................. G01F 1/66
[52] U.S. Cl. .............................. 73/194 A; 128/2.05 F
[58] Field of Search ................ 73/194 A; 128/2.05 F, 128/2.05 Z

[56] References Cited

U.S. PATENT DOCUMENTS

| 3,766,517 | 10/1973 | Fahrbach | 73/194 A |
| 3,987,673 | 10/1976 | Hansen | 73/194 A |

Primary Examiner—Charles A. Ruehl

[57] ABSTRACT

A crossed beam ultrasonic flowmeter particularly suited for measuring two dimensional arterial blood flow has two pairs of ultrasonic beam transmitting transducers the beams of which are focused to intersect at a predetermined region through which dynamic particles undergoing velocity analysis are moving. The transducers are preferably coplanar and disposed equiangularly about an axis with the predetermined region located therealong. A receiver is disposed adjacent the axis intermediate the beams for receiving the Doppler shifted scattered signal. Following squaring of the scattered signal, bandpass filters separate the spectrally separated scattered signals resulting from the two pairs of transducers which then undergo spectral analysis to determine the necessary frequency and velocity information. One of the four transducers may be utilized as a second receiver to determine the third velocity component with a filter separating the scattered signal resulting from the transducer disposed diametrically across the axis. Alternatively, a fifth transmitting transducer and second receiver are disposed on opposite sides of the axis with a filter separating the scattered signal resulting from the fifth transducer. A pair of perpendicular linear B-mode scanning transducer arrays intersect at and extend perpendicularly to the axis for obtaining sagittal and transverse B-mode images of a conduit carrying particles undergoing velocity analysis.

17 Claims, 6 Drawing Figures

CROSSED BEAM ULTRASONIC FLOWMETER

BACKGROUND OF THE INVENTION

Atherosclerosis is a widespread disease of the inner layers of arteries which results in regions of arterial narrowing and hardening, and the early detection of this disease prior to the appearance of overt symptoms is highly desirable to facilitate treatment.

A number of techniques are available for the measurement of arterial blood flow and thus the detection of atherosclerosis including electromagnetic, nuclear magnetic resonance, laser Doppler, X-ray with die injection, and ultrasonic Doppler techniques, the last providing the only method for noninvasive imaging of blood vessels.

Heretofore, however, Doppler ultrasound systems have not been capable of providing the desired velocity and spacial resolution in deep blood vessels, where many of the most harmful atherosclerotic lesions occur. Moreover, imaging deep blood vessels has previously required relatively high ultrasound exposure rates as the sensitivity of such systems is not sufficiently high. Accordingly, it is an object of the present invention to provide a novel ultrasonic flowmeter particularly suited for measuring blood flow which utilizes two pairs of crossed focused ultrasonic beams to provide improved sensitivity and velocity and range resolution.

It is also an object to provide such a flowmeter capable of measuring the three dimensional velocity vector of dynamic particles, particularly blood cells.

Another object is to provide such a flowmeter which is readily used in conjunction with a B-mode scanning device to provide information about the structure of and blood flow within a vessel.

SUMMARY OF THE INVENTION

It has now been found that the foregoing and related objects of the present invention are readily attained in a crossed beam ultrasonic flowmeter having first and second spaced ultrasonic beam transmitters driven by a continuous wave signal generator. A focusing means is connected to the transmitters to focus the beams thereof to intersect in a predetermined region through which dynamic particles undergoing velocity analysis are moving. The ultrasonic signal scattered from dynamic particles is received by a receiver and subsequently passes through a filter which separates the scattered ultrasonic signal for spectral analysis by a spectrum analyzer.

In the preferred aspect the two transmitters are driven at different frequencies and a squarer is connected in circuit relation to and intermediate the receiver and filter for squaring the scattered ultrasonic signal received from the receiver.

Also in the preferred embodiment, four coplanar transmitting transducers are disposed generally equiangularly about an axis with the diametrically opposed transducers functioning in pairs whereby two components of the velocity vector of a dynamic particle may be determined. The difference between the frequencies within one pair of transducers differs from the difference between the frequencies within the other pair of transducers. A focuser focuses the beams of all four transducers to intersect in a predetermined region with a receiving transducer disposed adjacent the axis receiving the ultrasonic signal scattered from dynamic particles undergoing velocity analysis, the signal from the receiving transducer is passed to a squarer for heterodyning and subsequently to filters for separating the spectrally separated scattered signals resulting from the two pairs of transmitting transducers. The separated signals then undergo spectral analysis to obtain the desired frequency and velocity information.

The flowmeter of the present invention may include a pair of perpendicular linear B-mode scanning transducer arrays intersecting at the aforementioned axis operable for obtaining sagittal and transverse B-mode images of a conduit carrying dynamic particles undergoing velocity analysis.

To determine the third component of the velocity of a dynamic particle, a fifth transmitting transducer is driven by the signal generator with the focuser directing the beam thereof to intersect the predetermined region, a second receiving transducer being disposed on the opposite side of the axis whereby the scattered signal received thereby passes to the squarer and then to a filter to separate the spectrally separated scattered signals resulting from the fifth transmitting transducer from those signals resulting from the two pairs of transmitting transducers.

Alternatively, the third velocity component may be determined by utilizing the two pairs of transmitting transducers as described hereinabove to ascertain two components of the velocity, then de-energizing one of the transmitting transducers to terminate the beam generated thereby whereby this transducer functions as a receiver. The scattered ultrasonic signal is detected by this receiver, filtered to separate the spectrally separated scattered signal resulting from the other of the pair of transducers one of which is now a receiver, and spectrally analyzed.

DETAILED DESCRIPTION OF THE ILLUSTRATED EMBODIMENT

Figure 1:
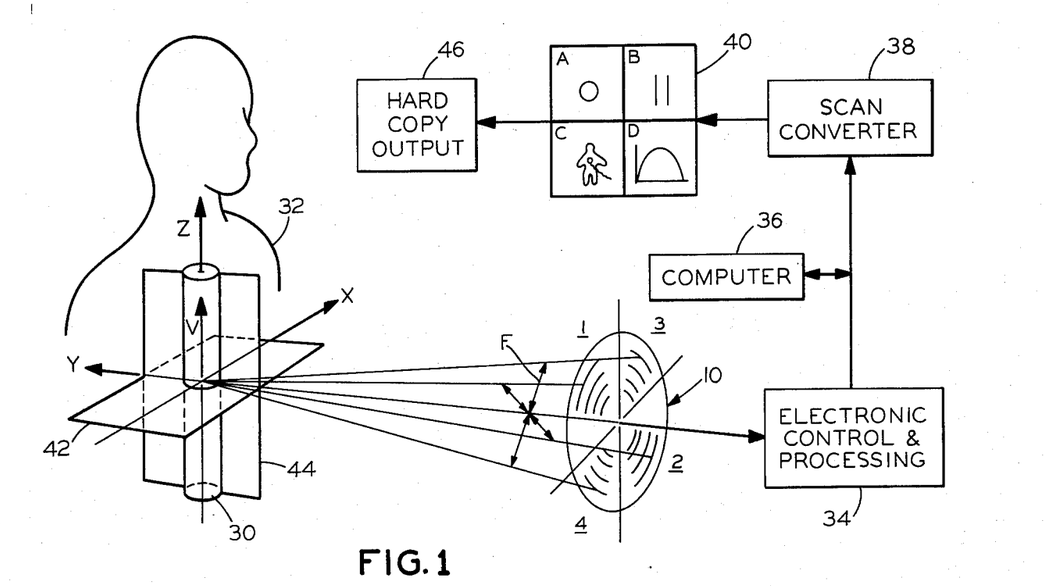
FIG. 1 is a diagrammatic illustration of a crossed beam ultrasonic flowmeter embodying the present invention showing a patient and blood vessel, the blood cells of which are undergoing velocity analysis.

Turning now to FIG. 1 of the attached drawings in detail, illustrated diagrammatically therein is a crossed beam ultrasonic flowmeter embodying the present invention comprising a circular transducer member generally designated by the numeral 10, various elements of which function as described hereinafter as a transmitter of two pairs of continuous wave focused crossed ultrasound beams, a receiver for scattered ultrasound from the pairs of beams, and a two dimensional sector scanner in conventional B-mode.

Figure 2:
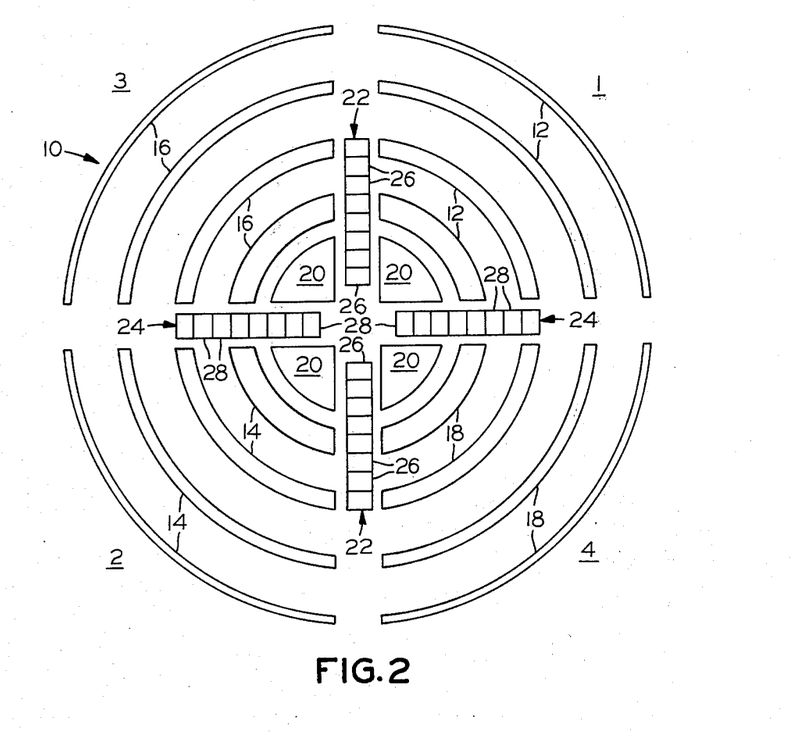
FIG. 2 is a diagrammatic illustration of the ultrasonic transmitting, receiving and B-mode scanning transducer array of the flowmeter of FIG. 1.

As shown in FIG. 2, the transducer member 10 is divided into four quadrants 1, 2, 3, 4 with each quadrant having four arcuate transmitting transducer elements 12,14,16,18 respectively. The elements 12,14,16,18 are capable of generating, with proper element phasing, four highly focused ultrasound beams with quadrants 1,2 and 3,4 working together to produce two orthogonal pairs of crossed beams, which pairs define different planes angularly spaced relative to a plane extending through the axis of flow through the vessel being studied. Four receiving transducer sectors 20 are disposed equiangularly about the center of the transducer member 10 with each of the sectors 20 lying in one of the quadrants 1,2,3,4 and are electrically coupled to function as a single receiver for scattered signals resulting from the transmitted crossed beams.

Disposed intermediate the quadrants 1,2,3,4 of the transducer member 10 are two orthogonal linear transducer arrays generally designated by the numerals 22,24, each comprising sixteen elements 26,28 respectively. The arrays 22,24 provide two dimensional electrically controlled sector scans in B-mode as described more fully hereinafter.

As shown in FIG. 1, the transducer member 10 is disposed for analysis of blood flow velocity V in a vessel 30 of a patient 32 undergoing examination. The transducer elements 12,14,16,18 are driven and focused as described hereinafter by the components of an electronic control and processing unit 34 which is controlled by a computer 36. The two pairs of crossed beams are focused to intersect in a region within the vessel 30, a standing wave being established in this region which is disturbed by blood cells moving therethrough which effect Doppler scattering of the ultrasound beams.

The ultrasound signal scattered from blood cells and received by the sectors 20 of the transducer member 10 is squared within the unit 34 to cause heterodyning and is filtered to separate the spectrally separated scattered signals emanating from quadrants 1,2 and 3,4. The filtered signal undergoes spectral analysis to determine the Doppler shifted frequencies and, as discussed in detail hereinafter, a velocity vector for blood flow in the region of beam intersection.

The computer 36 processes the frequency/velocity information which is then stored in a scan converter 38 for on-line display on a TV monitor 40 divided into four quadrants A,B,C,D. Quadrants A,B display the linear B-mode scans taken along a transverse plane 42 and sagittal plane 44 through the vessel 30, with quadrant C being conveniently taken by CCTV and showing the position of the transducer member 10 on the patient 32. Quadrant D displays a blood vessel velocity profile for the region of beam intersection. If so desired, a hard copy output 46 may be connected to the monitor 40. Moreover, the computer 36 may be utilized to generate alphanumerics which can be projected on the monitor 40 to identify instrument settings used in making the scans.

The flowmeter of the present invention has three basic operating modes, the first being utilization of two pairs of crossed ultrasound beams emanating from the transducer elements 12,14,16,18 which provide two dimensional and possibly three dimensional, depending on the initial orientation of the transducer member 10, velocity information. Secondly, the third velocity component may be determined in either of two ways. Eight contiguous elements 26,28 of one of the linear arrays 22,24 are utilized as a continuous wave ultrasound beam transmitter with the other eight elements 26,28 of the same array functioning as a receiver. Alternatively, transducer elements of one of the quadrants 1,2,3,4 of the transducer member 10 are utilized as a beam transmitter with the elements of the diametrically opposite quadrant functioning as a receiver. Third, the linear arrays 22,24 function in a manner known in the art to provide orthogonal transverse and sagittal plane sector scans in B-mode.

Figure 3:
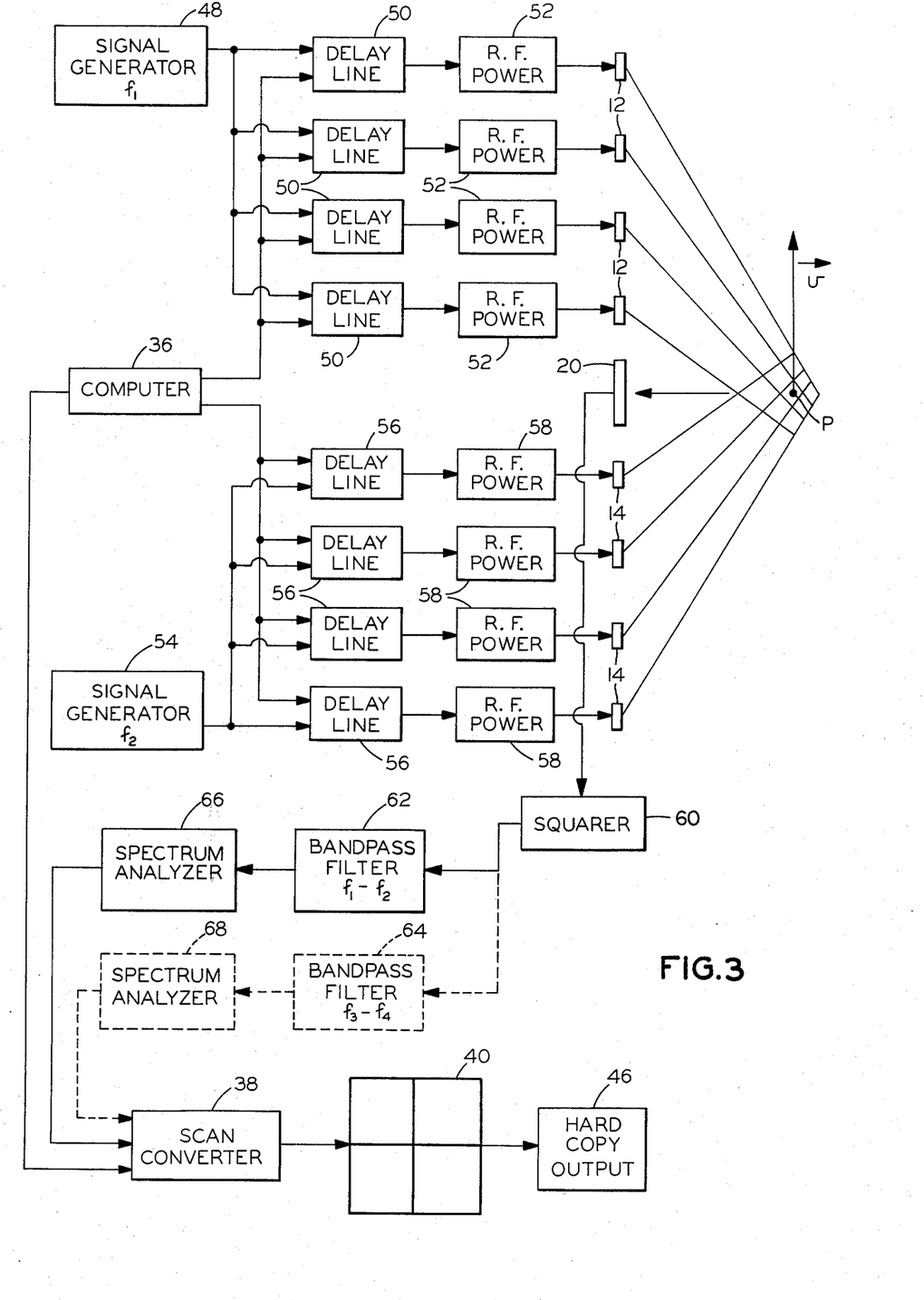
FIG. 3 is a diagrammatic illustration of a control and spectral analysis circuit for obtaining two dimensional velocity information for dynamic particles undergoing velocity analysis.

Turning to the mode of operation utilizing two pairs of crossed beams, a control and data processing circuit therefor is shown diagrammatically in FIG. 3. For purposes of clarity of illustration, the controls for only one pair of crossed beams are illustrated; the extension to two pairs is straightforward. The data processing units for the second pair of crossed beams are shown in broken line.

A sinusoid of frequency $f_1$ is directed to the several arcuate transducer elements 12 of the transducer member 10 by a signal generator 48 through four analog delay lines 50 which provide computer controlled phasing for electronic focusing of the beam transmitted by the elements 12. Final RF power stages 52 provide the necessary drive voltage for the elements 12. Final RF power stages 52 provide the necessary drive voltage for the elements 12. Similarly, a sinusoid of frequency $f_2$ is provided by a signal generator 54 which passes through focusing delay lines 56 for transmission by the several transducer elements 14, RF power stages 58 driving the elements 14. The crossed beams from transducer elements 12,14 (and 16,18) establish a standing wave which is disturbed by a dynamic particle P, such as a blood cell, moving therethrough, the particle P Doppler scattering ultrasound to the receiving transducer sectors 20.

The received backscattered is preamplified and squared in a squarer 60 to cause heterodyning of the composite backscattered signal from the four beams. Bandpass filters 62,64 separate the spectrally separated Doppler scattered components from the transmitting transducer elements 12,14 and 16,18. As discussed hereinafter, these two components are spectrally separated principally because of the initial condition that $|f_1-f_2| \neq |f_3-f_4|$, as the frequency of the scattered signal from each pair of beams is shifted relatively slightly from the frequency difference between the two beams of each pair. Thus, the filters 62,64 are set to pass frequencies within a predetermined deviation from the difference in frequencies within each pair of beams.

The filtered signals pass to spectrum analyzers 66,68 which determine the average Doppler shifted frequencies relative to the axes determined by lines connecting the centroids of the elements 12,14,16,18 of diametrically opposite quadrants 1,2 and 3,4 of the transducer member 10, and thus permit the calculation of velocity components along these two orthogonal axes. The resultant velocity information is further processed as described hereinbefore. With reference to FIG. 1 and the coordinate axes X,Y,Z centered at the base of the velocity vector V, the velocity information obtained as just described establishes the velocity of a particle in the X-Z plane.

The third velocity component may be determined in either of two ways as described in detail hereinafter in connection with the circuits of FIGS. 4 and 5. Alternatively, the transducer member 10 may be initially oriented to zero this third component (along the Y axis of FIG. 1) so that all the velocity information is in the X-Y plane velocity vector. To effectively zero the third velocity component the transducer member 10 is physically positioned so that the sagittal plane B-mode image indicates that the scan is being taken longitudinally of the vessel 30, that is, that the vessel 30 is parallel to the linear array 22 of the transducer member 10 (see quadrant B of the TV monitor 40 of FIG. 1). As discussed hereinafter, the backscattered Doppler shifted frequency when the flowmeter is set up to determine the third velocity component will be zero when the velocity of the particle P is parallel to the plane of the transducer member 10. Utilization of appropriate filtering will isolate this frequency, which can then be zeroed by physical manipulation of the transducer member 10.

Figure 4:
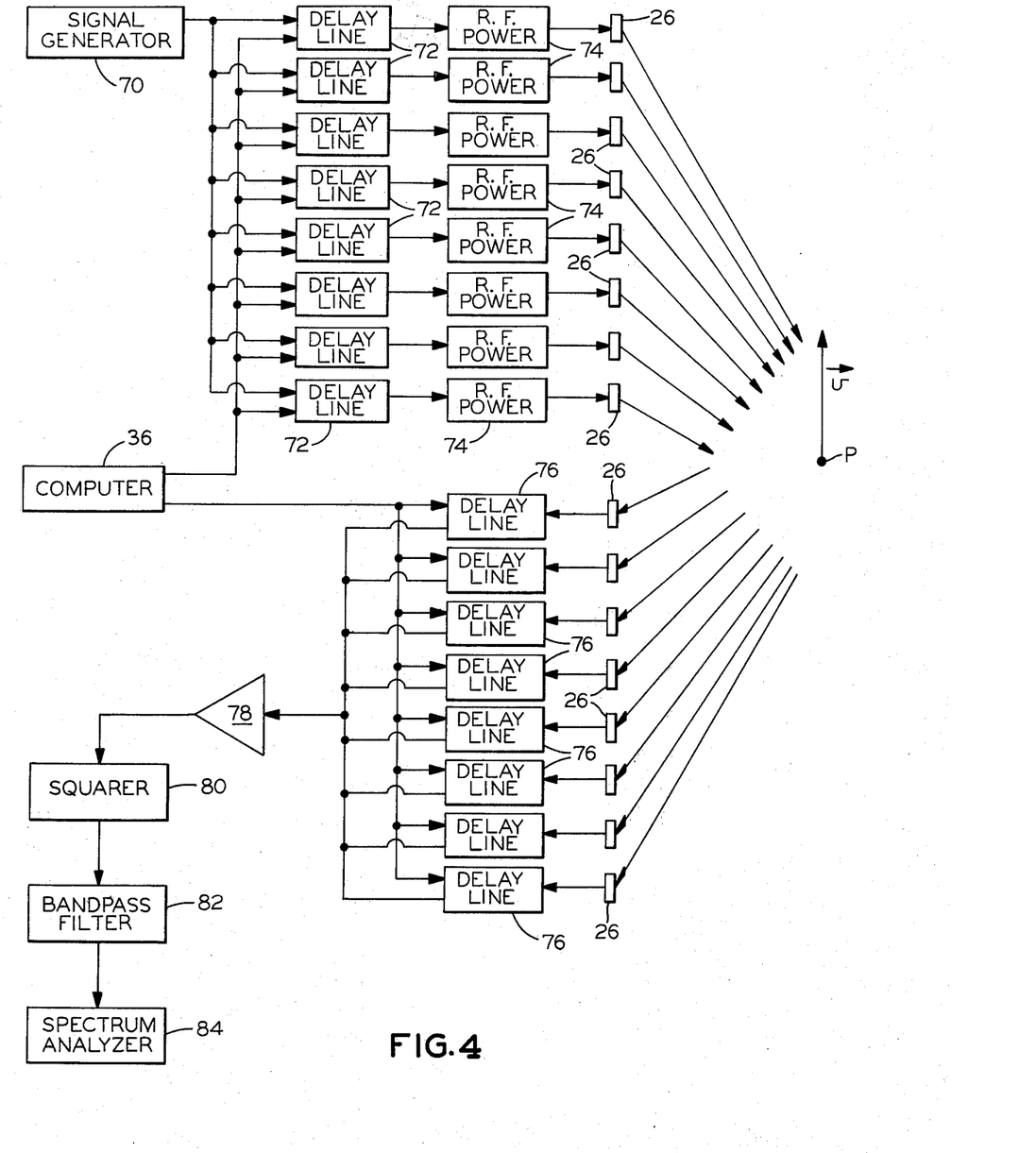
FIG. 4 is a diagrammatic illustration of a control and spectral analysis circuit for obtaining information relative to the third velocity component.

Turning now to FIG. 4 in detail, a signal generator 70 provides a sinusoid signal to eight computer controlled focusing delay lines 72, the output from the delay lines 72 passing to eight contiguous elements 26 of the linear transducer array 22 of the transducer member 10. RF power units 74 provide the necessary drive voltage for the elements 26. The sound scattered from the particle P is picked up by the other eight elements 26 of the array 22 and passes through delay lines 76 which compensate for the varying path lengths between the scatterer(s) and receiving elements 26. The outputs from the eight delay lines 72 are summed in a summer 78, the output of which is squared in a squarer 80, filtered in a bandpass filter 82 to separate the Doppler shifted signal resulting from the transmitting elements 26 of the array 22 which is spectrally separated from the scattered signals resulting from the two pairs of crossed beams. The signal is analyzed in a spectrum analyzer 84 to obtain the desired frequency, and thus velocity, information.

Figure 5:
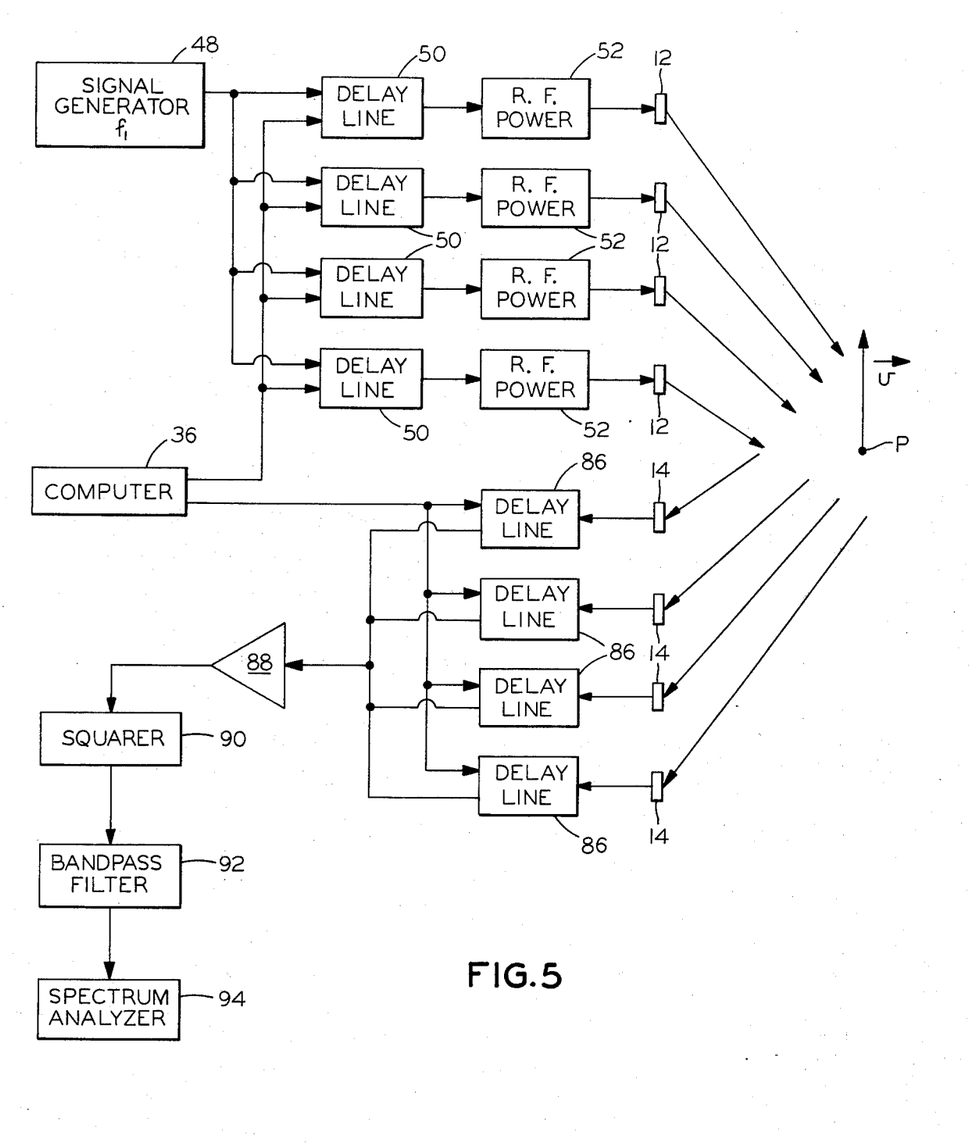
FIG. 5 is a diagrammatic illustration of another control and spectral analysis circuit for obtaining information relative to the third velocity component.

FIG. 5 illustrates diagrammatically the control and spectral analysis circuit for the second embodiment for obtaining the third velocity component. The signal generator 48 provides a sinusoid to the four arcuate transducer elements 12 of the transducer member 10 with delay lines 50 providing computer controlled phasing and focusing. RF power stages 52 provide the drive voltage for the elements 12. The scattered sound is received by the four transducer elements 14 diametrically opposed from the elements 12 with computer controlled delay lines 86 compensating for the path differences between the scatterer and receiving elements 14. As described hereinbefore in conjunction with the description of the circuit of FIG. 4, the output from the delay lines 86 passes to a summer 88, squarer 90, bandpass filter 92, and spectrum analyzer 94.

Figure 6:
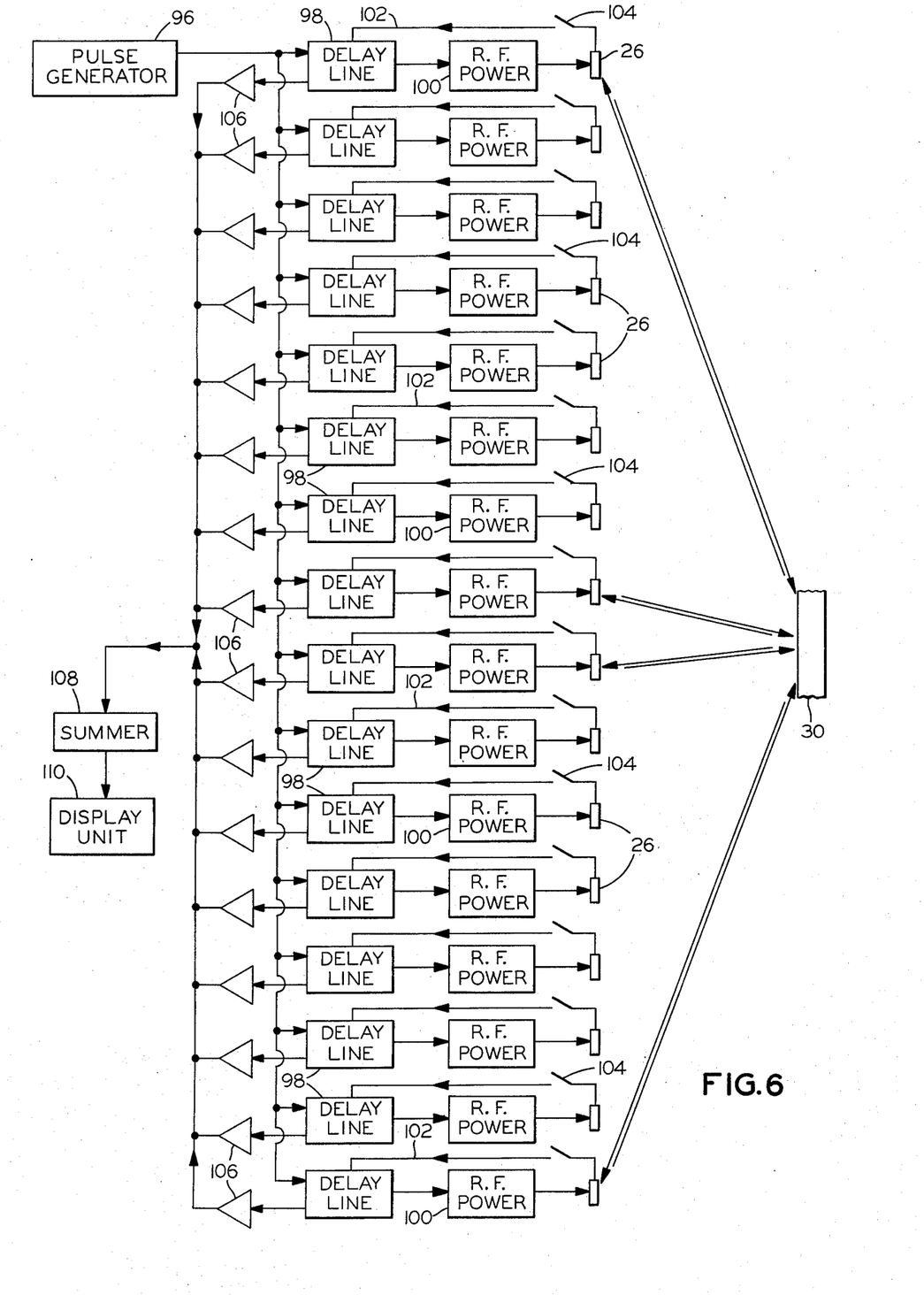
FIG. 6 is a diagrammatic illustration of a control and analysis circuit for the B-mode scanning transducers.

The control and analysis circuit for one of the B-mode scanning linear arrays 22,24 is shown in FIG. 6, it being understood that the extension to the two orthogonal arrays 22,24 is straightforward. In this mode, each of the sixteen elements 26 of the illustrated array 22 functions as both a transmitting and receiving transducer. A pulse generator 96 applies a pulse to each of the computer controlled (computer not shown) delay lines 98 which establish the time sequence between successive pulses. RF power units 100 provide the necessary drive voltage for the elements 26. The scattered pulses are received by the same sixteen elements 26 and pass back to the delay lines 98 through circuits 102 having computer controlled field effect transistor switches 104 therealong which are synchronized to pass the received signal. The delay lines 98 compensate for the path differences and the signal from each delay line 98 passes to a compression amplifier 106, a summer unit 108, and to an appropriate display and analyzing unit 110 which may include the TV monitor 40 shown in FIGS. 1 and 3.

The transducer member 10 is oriented initially to focus the pairs of crossed beams within the vessel 30 and, if desired, to align the transducer member 10 in parallel relationship with the vessel 30 by viewing the transverse and sagittal B-scan images of the vessel 30. The transverse plane image (see quadrant A of monitor 40) indicates whether the system is focusing at the desired depth within the patient 32 and the sagittal plane image (see quadrant B of monitor 40) indicates whether one of the linear arrays 22,24, and thus the transducer member 10, is parallel to the vessel 30.

It can be shown that the backscattered sound from a point scatterer passing through a region wherein a standing ultrasound wave has been established by a pair of crossed continuous wave ultrasound beams of frequencies $f_1$ and $f_2$ is a sinusoid having a frequency $f_D$ given by:

$$f_D = \left| \Delta f + \frac{2f \sin F}{c} \hat{k} \cdot \vec{v} \right|$$

$$\Delta f = f_1 - f_2$$

$$f = \frac{f_1 + f_2}{2}$$

F = angle between the transmitting transducer centroid and the normal to the sensitivity vector $\vec{k}$ as defined below, or half the angle between the two intersecting beams c = velocity of sound in the medium $\vec{v}$ = velocity vector of the point scatterer(s)

$\hat{k} = \vec{k}/|\vec{k}|$ where $\vec{k}$ is the vector difference between the wave vectors of the two incident beams For frequencies on the order of 3 MHz, which is near the primary resonance of the transducer material used, $\Delta f$ is designed to be on the order of 20–40 KHz with the magnitude of the second term in the expression for $f_D$ being substantially smaller. Thus, the bandpass filters 62,64 of the circuit of FIG. 3 are set to pass frequencies within a preset deviation from $\Delta f$, with $|f_1-f_2|$ differing from $|f_3-f_4|$ by an amount sufficient to separate spectrally the two $f_D$ values resulting from the two pairs of crossed beams. Due to the idealized geometry of FIG. 1 where the linear array 22 is parallel to the Z axis and the transducer member 10 is parallel to the X-Z plane, the wave vector $\vec{k}$ will lie in the X-Z plane and thus the formula for $f_D$ yields the component of the velocity vector lying in that plane. If, as illustrated, the velocity vector lies along the Z axis, the X-Z plane component provides complete velocity information.

With reference to the control circuits of FIGS. 4 and 5 and the determination of the third velocity component, it can be shown that the backscattered ultrasound from a point of scatterer resulting from a single ultrasound beam of frequency $f$ is a sinusoid of frequency $f_D$ given by:

$$f_D = \left| \frac{2f \sin F}{c} \hat{k} \cdot \vec{v} \right|$$

where F, c and $\vec{v}$ are as defined above $\hat{k} = \vec{k}/|\vec{k}|$ where $\vec{k}$ is the vector difference between the wave vectors of the incident and scattered beams.

Since the magnitude of this expression for $f_D$ is significantly less than $\Delta f$ from the previously discussed equation for $f_D$, this frequency component is easily separated from the crossed beam Doppler scattered sound. Referring to the geometry of FIG. 1, $\vec{k}$ will lie along the Y axis and thus this expression for $f_D$ yields the projection of the velocity vector (if any) on the Y axis.

The first expression for $f_D$, utilizing a pair of crossed beams, indicates that $f_D$ is independent of the location of the receiving transducer as they are derived assuming that the receiver is disposed at an arbitrary point intermediate the crossed beams. Thus, the frequency shift or $f_D$ is dependent only on the orientation of the two transmitting transducers of each pair relative to the velocity vector. Moreover, the system is direction sensitive in the crossed beam mode as the second term in the expression for $f_D$ will be either positive or negative depending on the relative orientations of $\vec{k}$ and $\vec{v}$.

The flowmeter is sensitive only to Doppler shifts produced by particle scattering in the region of intersection of the highly focused beams even though operation is in the continuous wave mode, this region of intersection being on the order of a millimeter on a side. Thus, range resolution is achieved without sacrificing velocity resolution. Furthermore, since a receiving transducer placed between two crossed beams picks up a Doppler shifted frequency which depends only on the angles of the two crossed beams relative to the direction of the velocity vector, the receiving transducer can be made as large as possible to pick up all the scattered sound energy, resulting in an improved sensitivity and signal-to-noise ratio.

The velocity resolution in a continuous wave Doppler system is limited by the transit time of the particles through the ultrasonic field, or in the case of pulsatile flow, by the time varying nature of the flow. It can be shown that for transmit frequencies on the order of 5 MHz, the velocity resolution for a crossed beam system for slow varying flow such as in peripheral arteries is about 0.5 cm/sec and for rapid flow such as in the ascending aorta about 3.5 cm/sec.

The transducer member is formed of a 2.5 MHz primary resonance circular plate of lead zirconate titanate which is scribed in a known manner to provide the isolated piezoelectric elements as shown in FIG. 2. While the transducer member is preferably as illustrated and described, the transmitting, receiving and B-mode elements thereof may be formed, for example, of distinct piezoelectric members and have different configurations so long as the focused crossed beam pattern is attainable.

The control and data processing elements are preferably as described, but may consist of different elements so long as the Doppler shifted frequencies may be isolated from the total scattered signal and noise. The flowmeter may be used without a squarer, but if so the Doppler frequency is dependent upon the position of the receiver. Furthermore, although it is preferable that the transmitting transducers in each pair operate at different frequencies, they may be driven at the same frequency if the directionality of the particle velocity need not be ascertained.

The disposition of the receiver is preferably along a line extending perpendicularly through the center of the transducer member for maximum sensitivity, although it may be located other than on this line if so desired. The centroids of the transmitting transducer arrays are located equiangularly about the center of the transducer member and equidistantly therefrom to provide information relative to orghogonal velocity components and to simplify the mathematical expressions for $f_D$.

Thus, it can be seen that the present invention provides a novel crossed beam ultrasonic flowmeter particularly suited for measuring blood flow which utilizes two pairs of crossed focused ultrasonic beams to provide improved sensitivity and velocity and range resolution. The flowmeter is capable of measuring the three dimensional velocity vector of dynamic particles, and is readily used in conjunction with a B-mode scanning device to provide information about the structure of and blood flow within a vessel.

Having thus described the invention, I claim:

1. A crossed beam ultrasonic flowmeter comprising:
  A. first and second spaced ultrasonic beam transmitting means providing a first cooperating pair of intersecting ultrasonic beams;
  B. third and fourth ultrasonic beam transmitting means spaced apart and from said first and second ultrasonic beam transmitting means, said third and fourth transmitting means providing a second pair of intersecting ultrasonic beams;
  C. signal generating means connected in circuit relation to said transmitting means for driving said first transmitting means at a first ultrasonic frequency and said second transmitting means at a second ultrasonic frequency and for driving said third transmitting means at a frequency differing from that of said fourth transmitting means, the difference in frequency between said first and second transmitting means differing by a predetermined amount from the difference between the frequencies of said third and fourth transmitting means;
  D. focusing means connected to said transmitting means for focusing the beams of each pair of said transmitting means to intersect in a predetermined region through which dynamic particles undergoing velocity analysis are moving, the focused beams of said third and fourth transmitting means defining therebetween a plane disposed at an angle to the plane defined between said focused beams of said first and second transmitting means;
  E. receiving means for receiving the ultransonic signal scattered from dynamic particles undergoing velocity analysis;
  F. filter means connected in circuit relation to said receiving means for separating the scattered ultrasonic signals received from said receiving means, said filter means separating the spectrally separated scattered ultrasonic signals resulting from said first and second and from said third and fourth transmitting means; and
  G. spectrum analysis means connected in circuit relation to said filter means for analyzing said scattered ultrasonic signal.

2. The flowmeter of claim 1 wherein said signal generating means drives said transmitting means in a continuous wave mode, said first frequency differs from said second frequency, and further including heterodyning means connected in circuit relation to and intermediate said receiving means and said filter means for squaring said scattered ultrasonic signal received from said receiving means.

3. The flowmeter of claim 1 wherein said transmitting means and said receiving means comprise transducer means.

4. The flowmeter of claim 1 wherein said receiving means is disposed adjacent the line of intersection of said first mentioned and second mentioned planes at a point intermediate said beams of said transmitting means.

5. The flowmeter of claim 1 wherein said first mentioned plane is perpendicular to said second mentioned plane.

6. The flowmeter of claim 1 further including a pair of perpendicular linear B-mode scanning means operable for obtaining sagittal and transverse B-mode images of a conduit carrying dynamic particles undergoing velocity analysis.

7. The flowmeter of claim 1 further including fifth ultrasonic beam transmitting means connected in circuit relation to said signal generating means and second receiving means for receiving the ultrasonic signal scattered from dynamic particles undergoing velocity analysis connected in circuit relation to said heterodyning means, said focusing means being connected to said fifth transmitting means for focusing the beam thereof to intersect said predetermined region, said fifth transmitting means and said second receiving means being disposed on opposite sides of the line of intersection of said first mentioned and second mentioned planes, and said filter means separating the spectrally separated scattered ultrasonic signals resulting from said first and second, said third and fourth, and said fifth transmitting means.

8. The flowmeter of claim 7 wherein said planes are perpendicular and said receiving means is disposed adjacent the line of intersection of said planes.

9. A crossed beam ultrasonic flowmeter comprising:
A. first, second, third and fourth ultrasonic beam transmitting transducers disposed generally equiangularly and numerically consecutively about an axis;
B. continuous wave signal generating means connected in circuit relation to said transducers for driving said transducers at predetermined frequencies, the difference between the frequencies of said first and third transducers differing from the difference between the frequencies of said second and fourth transducers;
C. focusing means connected to said transducers for focusing the beams thereof to intersect in a predetermined region along said axis through which region dynamic particles undergoing velocity analysis are moving, said transmitting transducers being disposed about said axis on one side of said region;
D. a receiving transducer disposed adjacent said axis intermediate said beams of said transmitting transducers for receiving the ultrasonic signal scattered from dynamic particles undergoing velocity analysis;
E. heterodyning means connected in circuit relation to said receiving means for squaring the ultrasonic signal received from said receiving means;
F. filter means connected in circuit relation to said heterodyning means operable to separate the spectrally separated scattered ultrasonic signals resulting from said first and third, and said second and fourth transducers; and
G. spectrum analysis means connected in circuit relation to said filter means for analyzing said scattered ultrasonic signals.

10. The flowmeter of claim 9 wherein said transducers and said receiving means are disposed in a plane perpendicular to said axis.

11. The flowmeter of claim 10 further including a pair of perpendicular linear B-mode scanning means intersecting at and extending perpendicularly to said axis operable for obtaining sagittal and transverse B-mode images of a conduit carrying dynamic particles undergoing velocity analysis.

12. A method for measuring the velocity of a dynamic particle wherein the steps comprise:
A. mounting first, second, third and fourth transducer means in spaced relation and numerically consecutively about an axis;
B. energizing said first and third transducer means to propagate a first pair of continuous wave ultrasonic beams having different frequencies;
C. energizing said second and fourth transducer means to propagate a second pair of continuous wave ultrasonic beams having different frequencies with the difference in frequencies between said first pair of transducer means differing from the difference in frequencies between said second pair of transducer means;
D. focusing said beams of said transducer means to intersect in a predetermined region along said axis through which dynamic particles undergoing velocity analysis are moving, the focused beams of said first and third transducer means and said second and fourth transducer means defining a pair of planes intersecting at a predetermined angle;
E. detecting, heterodyning, and filtering the ultrasonic signal scattered from dynamic particles undergoing velocity analysis to separate the spectrally separated scattered signal resulting from said first and third, and said second and fourth transducer means;
F. de-energizing said first transducer means to terminate the beam generated thereby whereby said first transducer means functions as an ultrasonic receiver;
G. detecting with said first transducer means the ultrasonic signal scattered from dynamic particles undergoing velocity analysis;
H. filtering said ultrasonic signal to separate the spectrally separated scattered ultrasonic signal resulting from said third transducer means; and
I. analyzing the spectrum of the filtered ultrasonic signal to obtain the desired frequency information.

13. A crossed beam ultrasonic flowmeter comprising:
A. at least one pair of cooperating, spaced ultrasonic beam transmitting means, each of said ultrasonic beam transmitting means being comprised of a multiplicity of separate transducing elements arranged in a predetermined array;
B. signal generating means connected in circuit relation to said transmitting means for driving one transmitting means of the pair at a first ultrasonic frequency and the other transmitting means of the pair at a second ultrasonic frequency;
C. electronic focusing means connected to the several transducing elements of each of said transmitting means for focusing the beams of said transmitting means to intersect in a predetermined region through which dynamic particles undergoing velocity analysis are moving and to limit the ultrasonic volume in the predetermined region;
D. receiving means for receiving the ultrasonic signal scattered from dynamic particles undergoing velocity analysis;

E. filter means connected in circuit relation to said receiving means for separating the scattered ultrasonic signal received from said receiving means; and F. spectrum analysis means connected in circuit relation to said filter means for analyzing said scattered ultrasonic signal.

14. The flowmeter of claim 13 wherein said electronic focusing means includes ultrasonic delay lines.

15. The flowmeter of claim 13 wherein said flowmeter includes at least two pairs of ultrasonic beam transmitting means and wherein the plane defined by the second pair of transmitting means intersects the plane defined by the first pair of transmitting means, and wherein the difference in frequencies between the transmitting means of the second pair is different from the difference in frequencies between the first pair of transmitting means.

16. The flowmeter of claim 15 wherein said filter means separates the spectrally separated scattered ultrasonic signals resulting from the first pair and from the second pair of transmitting means.

17. The flowmeter of claim 13 wherein said signal generating means drives said transmitting means in a continuous wave mode, said first frequency differs from said second frequency, and further including heterodyning means and said filter means for squaring said scattered ultrasonic signal received from said receiving means.

* * * * *